United States Patent
Lopez Baca et al.

(10) Patent No.: US 11,642,295 B2
(45) Date of Patent: May 9, 2023

(54) PERSONAL CARE COMPOSITIONS AND METHODS FOR IMPROVING CURL RETENTION IN HAIR

(71) Applicant: Colgate-Palmolive Company, New York, NY (US)

(72) Inventors: Ramon Arnoldo Lopez Baca, Edo de Mex (MX); Cesar Higareda, Mexico City (MX); Maria de Lourdes Curiel Rodriguez, Tecámac (MX)

(73) Assignee: Colgate-Palmolive Company, New York, NY (US)

( * ) Notice: Subject to any disclaimer, the term of this patent is extended or adjusted under 35 U.S.C. 154(b) by 95 days.

(21) Appl. No.: 16/772,197

(22) PCT Filed: Dec. 15, 2017

(86) PCT No.: PCT/US2017/066565
§ 371 (c)(1),
(2) Date: Jun. 12, 2020

(87) PCT Pub. No.: WO2019/117934
PCT Pub. Date: Jun. 20, 2019

(65) Prior Publication Data
US 2021/0069080 A1    Mar. 11, 2021

(51) Int. Cl.
*A61Q 5/00* (2006.01)
*A61K 8/41* (2006.01)
*A61Q 5/12* (2006.01)

(52) U.S. Cl.
CPC ............... *A61K 8/416* (2013.01); *A61Q 5/12* (2013.01); *A61K 2800/31* (2013.01)

(58) Field of Classification Search
None
See application file for complete search history.

(56) References Cited

U.S. PATENT DOCUMENTS

| | | | |
|---|---|---|---|
| 7,056,350 B1 | 6/2006 | Wohlman et al. | |
| 7,608,569 B2 | 10/2009 | Nguyen et al. | |
| 8,367,047 B2 | 2/2013 | Nguyen et al. | |
| 8,475,778 B2 | 7/2013 | Nguyen et al. | |
| 9,622,945 B2 | 4/2017 | Garrison et al. | |
| 2004/0101505 A1 | 5/2004 | Payne et al. | |
| 2005/0069517 A1 | 3/2005 | Lim et al. | |
| 2009/0252689 A1* | 10/2009 | Collin | C08F 2/26 424/47 |
| 2012/0021025 A1 | 1/2012 | Bendejacq et al. | |
| 2012/0107259 A1* | 5/2012 | Cen | A61Q 13/00 424/70.28 |
| 2012/0114584 A1 | 5/2012 | Woghiren et al. | |
| 2015/0050230 A1 | 2/2015 | Yang et al. | |
| 2017/0239167 A1 | 8/2017 | Baca et al. | |
| 2017/0246102 A1 | 8/2017 | Baca et al. | |

OTHER PUBLICATIONS

Becker, Tonya Mckay, "Elasticity and Healthy Hair," published Mar. 6, 2011, pp. 1-3, URL: https://www.naturallycurly.com/curlreading/wavy-hair-type-2/elasticity-and-healthy-hair, retrieved Feb. 26, 2021.
Elementis Specialties, Inc., "Personal Care Formulary," Published Mar. 28, 2014, pp. 1-20. URL: www.essentialingredients.com, retrieved Feb. 26, 2021.
Avon, 2015, "Conditioner," Mintel Database GNPD AN: 2962225.
International Search Report and Written Opinion of the International Searching Authority in International Application No. PCT/US2017/066565, dated Jul. 6, 2018.
Kert Ind. E Com. De Cosmeticos, 2015, "3X Conditioner," Mintel Database GNPD AN: 3336483.
Kert Ind. E. Com. De Cosmeticos, 2015, "3X Shampoo," Mintel Database GNPD AN: 3336481.

* cited by examiner

*Primary Examiner* — Jyothsna A Venkat

(57) ABSTRACT

Hair care compositions and methods for improving curl retention of hair are provided. The hair car composition may include a carrier and a quaternary ammonium compound. The method for improving curl retention may include contacting the hair care composition with surfaces of the hair of a subject in need thereof.

6 Claims, No Drawings

PERSONAL CARE COMPOSITIONS AND METHODS FOR IMPROVING CURL RETENTION IN HAIR

BACKGROUND

Conventional hair care products and hair care compositions thereof (e.g., shampoos and conditioners) often include one or more beneficial ingredients or components to impart one or more benefits or properties to hair. For example, shampoos and conditioners often include beneficial components to improve curl retention and reduce frizziness. While conventional beneficial components or benefits agents have sufficiently improved curl retention or curl definition and reduced frizziness, exposure to relatively high humidity often reduces the overall effectiveness of these benefit agents.

What is needed, then, are improved hair care products and methods for reducing frizziness, and improving curl retention or curl definition.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

Embodiments of the disclosure may provide a hair care composition for improving curl retention of hair. The hair care composition may include a carrier and a quaternary ammonium compound configured to improve curl retention of hair. The quaternary ammonium compound may be represented by formula (1).

In at least one embodiment, the counterion of the quaternary ammonium compound is selected from a halide ion, a sulfate ion, a phosphate ion, a methosulfate ion, or an organic ion.

In at least one embodiment, the quaternary ammonium compound may be represented by formula (2).

In at least one embodiment, the quaternary ammonium compound may be present in an amount of from about 0.05 weight % to about 7 weight %, based on a total weight of the hair care composition.

In at least one embodiment, the carrier may include at least one of surfactants, colorants, denaturants, film forming polymers, conditioning agents, fixatives, hair color stabilizers, anti-inflammatory agents, antioxidants, moisturizers, enzymes, proteins, protein hydrolizates or hydrolysates, amino acids, vitamins, minerals, natural extracts, antidandruff agents, sunscreen agents, and mixtures thereof.

In at least one embodiment, the carrier is anhydrous.
In at least one embodiment, the carrier is hydrophilic.
In another embodiment, the carrier is hydrophobic.

Embodiments of the disclosure may also provide a method for improving curl retention in hair of a subject. The method may include contacting any one of the hair care compositions disclosed herein with surfaces of the hair of the subject in need thereof.

In at least one embodiment, the hair contacted with the hair care composition exhibits relatively less change in curl volume as compared to hair treated with a hair care composition without the quaternary ammonium compound.

Embodiments of the disclosure may further provide a method for preparing any of the hair care compositions disclosed herein. The method may include contacting the quaternary ammonium compound with the carrier.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10° % (inclusive) of that numeral, or ±15% (inclusive) of that numeral. It should further be appreciated that when a numerical range is disclosed herein, any numerical value falling within the range is also specifically disclosed.

Compositions

Compositions disclosed herein may be or include a personal care product or a personal care composition thereof. The personal care composition may be a leave-in or leave-on composition (e.g., leave-in or leave-on hair conditioner) or a rinse-off composition (e.g., rinse-off hair conditioner). The personal care composition may be or include a hair care product or a hair care composition thereof. Illustrative hair care products may be or include, but are not limited to, shampoos, leave-in or rinse-off conditioners, leave-in or rinse-off deep treatments, hair spray, gels, or the like. In an exemplary implementation, the composition is a leave-in or a rinse-off conditioner. As further described herein, the composition may include a quaternary ammonium compound and a vehicle or carrier.

Personal Care Vehicle or Carrier

In at least one implementation, the personal care product or the composition thereof may be a hair care composition or a hair care product, such as a hair conditioner, and may include a quaternary ammonium compound dispersed in, mixed with, combined with, or otherwise contacted with a vehicle or carrier. In at least one implementation, the carrier may be capable of or configured to store, entrain, or otherwise contain the quaternary ammonium compound, and deliver the quaternary ammonium compound to surfaces of hair.

The carrier may include any one or more further ingredients that are suitable for inclusion into the composition for use on hair of a mammal or human. As used herein, the expression "one or more further ingredients that are suitable for inclusion in the composition for use on the hair of a mammal or human" may refer to any one or more ingredients or components that are characteristic of a hair care product, such as a hair conditioner. The carrier disclosed herein may also include ingredients or components that are not necessarily characteristic of a hair care product in combination with at least one ingredient or component that is characteristic of a hair care product.

The carrier for the hair care composition may include, but is not limited to, any one or more of the following: surfactants, viscosity enhancers or control agents, pH modifiers (e.g., acids, bases, buffers, etc.), emulsifiers, oils, fatty alcohols, silicones, cationics, detangling agents, hair shine enhancers, hair strengtheners, preservatives, fragrances, thickeners, rheology modifiers, colorants, denaturants, film forming polymers, conditioning agents, fixatives, hair color stabilizers, anti-inflammatory agents, antioxidants, moisturizers, enzymes and other proteins including protein hydrolizates or hydrolysates, amino acids, vitamins, minerals, natural extracts, antidandruff agents, sunscreen agents, and mixtures thereof.

Illustrative conditioning agents may include, but are not limited to, any one or more of silicones (e.g., silicone oils, cationic silicones, silicone gums, high refractive silicones, silicone resins, etc.), and organic conditioning oils (e.g., hydrocarbon oils, polyolefins, fatty esters, etc.).

Illustrative anti-dandruff agents may include, but are not limited to, pyridinethione salts, selenium sulfide, particulate sulfur, and the like, and mixtures thereof.

Illustrative anti-inflammatory agents may include, but are not limited to, glucocorticoids, nonsteroidal anti-inflammatories, and the like, and mixtures or combinations thereof.

Illustrative colorants may include, but are not limited to, non-oxidative dyes, such as "direct action dyes," metallic dyes, metal chelate dyes, fiber/fibre reactive dyes, other synthetic and natural dyes, and the like, and mixtures or combinations thereof.

Illustrative sunscreen agents may include, but are not limited to, 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylme-thane, 4-isopropyl dibenzoylmethane, 3-benzylidene camphor, 3-(4-methylbenzylidene) camphor, titanium dioxide, zinc oxide, silica, iron oxide, and the like, and mixtures or combinations thereof.

Illustrative vitamins may include, but are not limited to, Vitamin E, panthenol, and the like, and mixtures or combinations thereof.

Illustrative fatty alcohols may include, but are not limited to, stearyl alcohol, cetyl alcohol, or the like, or mixtures and combinations thereof.

Illustrative silicones may include, but are not limited to, dimethicone, dimethiconol, amodimethicone, cyclopentasiloxane, or the like, or any combination thereof.

Illustrative cationics may include, but are not limited to, surfactants such as cetrimonium chloride, behentrimonium methosulfate, behenamidopropyl dimethylamine, or quaternium 82, or polymeric cationics, such as the polyquarternium series (e.g., polyquarternium-6, -7, or -8), cationic guar gum, or the like, or mixture and combinations thereof. Further examples of fatty alcohols, silicones, and cationics are known to those skilled in the art of formulating hair care products and hair care compositions thereof.

The carrier may be hydrophilic or hydrophobic. The carrier may be anhydrous. The carrier may be a liquid or a solid at room temperature. The carrier may have a viscosity of from about 2,000 centipoise (cP) to about 100,000 cP. For example, the carrier for a shower gel may have a viscosity of from about 2,000 cP to about 16,000 cP. In another example, the carrier for a lotion may have a viscosity of from about 10,000 cP to about 100,000 cP. Accordingly, it should be appreciated that the viscosity of the carrier may vary and may at least partially depend on the type of personal care composition.

Quaternary Ammonium Compound

The quaternary ammonium compound may be a cationic material represented by formula (1):

(1)

where:
R$_1$ may be independently selected from: a $C_{10}$-$C_{22}$ alkyl group, a $C_{10}$-$C_{22}$ ester group, $R_5$—C(=O)NH(CH$_2$)$_m$ group, where $R_5$ may be $C_{10}$-$C_{22}$ alkyl, where m is an integer from 1 to 3, and mixtures thereof;

R$_2$ and R$_4$ may each be independently selected from: H, $C_1$-$C_5$ alkyl and polyoxyalkylene groups having polyalkylene repeating units containing from 1 to 4 carbon atoms;

R$_3$ may be independently selected from R$_1$, R$_2$, and R$_4$; and

X$^-$ is an anion.

In at least one implementation, the R$_1$ and R$_2$ groups may be derived from naturally occurring fats or oils such as tallow, soybean oil, coconut oil, cottonseed oil, castor oil, safflower oil, meadowfoam seed oil, abyssinia oil, or the like, or mixtures and combinations thereof. In another implementation, the polyoxyalkylene group may include: an oxyethylene having the structure —(OCH$_2$CH$_2$); an oxypropylene having the structure —(OCH(CH$_3$)H$_2$)— or —(OCH$_2$(CH)CH$_3$)—; an oxytrimethylene having the structure —(OCH$_2$CH$_2$CH$_2$)—; and/or a 1,4-oxybutylene having the structure —(OC$_4$H$_8$)—.

The counterion (X$^-$) of the cationic material may be any suitable cation. Illustrative cations may be or include, but are not limited to, halide ions, sulfate ions, phosphate ions, methosulfate ions, organic ions, and other anions, or the like, or mixtures and combinations thereof. Illustrative organic ions may include, but are not limited to, lactate, citrate, tartrate, acetate, or the like, or combinations thereof.

In an exemplary implementation, the quaternary ammonium compound may be a PEG-2 dimeadowfoamamidoethylmonium represented by formula (2), which is commercially available from Elementis Specialties Inc. of Livingston, UK under trade name MEADOWQUAT® HG-70.

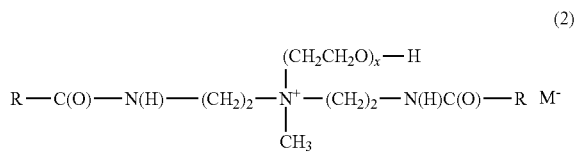

(2)

where R may have the following composition:
about 6 to about 65 weight % —(CH$_2$)$_3$—CH=CH—(CH$_2$)$_{13}$—CH$_3$;
about 12 to about 20 weight % a mixture of —(CH$_2$)$_3$—CH=CH—(CH$_2$)$_{15}$—CH$_3$ and —(CH$_2$)$_{11}$—CH=CH—(CH$_2$)$_7$—CH$_3$; and
x may be 2; and
M$^-$ may be SO$_4$CH$_3$.

The amount or concentration of the quaternary ammonium compound may vary widely. In at least one implementation, the quaternary ammonium compound may be present in an amount of from about 0.05 weight % to about 7 weight %, based on a total weight of the personal or hair care composition. For example, the quaternary ammonium compound may be present in an amount of from about 0.05 weight %, about 0.1 weight %, about 0.15 weight %, about 0.2 weight %, about 0.3 weight %, about 0.4 weight %, about 0.5 weight %, about 1 weight %, about 1.5 weight %, about 2 weight %, about 2.5 weight %, about 3 weight %, or about 3.5 weight % to about 4 weight %, about 4.5 weight %, about 5 weight %, about 5.5 weight %, about 6 weight %, about 6.5 weight %, or about 7 weight %. In another example, the quaternary ammonium compound may be present in an amount of less than or equal to less than or equal to 0.05 weight %, less than or equal to 0.1 weight %, less than or equal to 0.15 weight %, less than or equal to 0.2 weight %, less than or equal to 0.3 weight %, less than or equal to 0.4 weight %, less than or equal to 0.5 weight %, less than or equal to 1 weight %, less than or equal to 1.5 weight %, less than or equal to 2 weight %, less than or equal to 2.5 weight %, less than or equal to 3 weight %, less than or equal to 3.5 weight %, less than or equal to 4 weight %, less than or equal to 4.5 weight %, less than or equal to 5 weight %, less than or equal to 5.5 weight %, less than or equal to 6 weight %, less than or equal to 6.5 weight %, or less than or equal to 7 weight %. In yet another example, the quaternary ammonium compound may be present in an amount of about 0.05 weight % to about 7 weight %, about 0.1 weight % to about 6.5 weight %, about 0.15 weight % to about 6 weight %, about 0.2 weight % to about 5.5 weight %, about 0.3 weight % to about 5 weight %, about 0.4 weight % to about 4.5 weight %, about 0.5 weight % to about 4 weight %, about 1 weight % to about 3.5 weight %, about 1.5 weight % to about 3 weight %, or about 2 weight % to about 2.5 weight %.

Unless otherwise specifically identified, the ingredients for use in the compositions and formulations of the present invention are preferably cosmetically acceptable ingredients. By "cosmetically acceptable" is meant suitable for use in a formulation for topical application to human skin. A cosmetically acceptable excipient, for example, is an excipient that is suitable for external application in the amounts and concentrations contemplated in the formulations of this invention, and includes for example, excipients that are "Generally Recognized as Safe" (GRAS) by the United States Food and Drug Administration.

Methods

The present disclosure may include methods for using the personal care or hair care composition including the quaternary ammonium compound that results in improved or increased curl retention and/or reduced frizziness when applied to a surface (e.g., keratin surface) of hair. The method may include applying to the hair of a mammal or human in need thereof a personal care composition including a carrier and a quaternary ammonium compound.

The present disclosure may also include a use of a composition including a quaternary ammonium compound for improving or increasing curl retention and/or reducing frizziness.

The present disclosure may further include methods for making a hair care composition for improving or increasing curl retention and/or reducing frizziness. The method may include combining or otherwise contacting a quaternary ammonium compound with a carrier.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The curl definition as determined by frizziness or control of frizz of hair treated with a hair care composition including a quaternary ammonium compound was evaluated. Particularly, a control hair care composition (1) and a hair care composition including a quaternary ammonium compound, namely, PEG-2 dimeadowfoam-amidoethylmonium methosulfate, (2) were prepared according to Table 1 and evaluated.

TABLE 1

Hair Care Compositions of Control (1) and Test (2)

| INGREDIENT/COMPONENT | CONTROL (1) (% WEIGHT) | TEST (2) (% WEIGHT) |
| --- | --- | --- |
| Purified Water | Q.S. | Q.S. |
| Thickener | 0.03 | 0.03 |
| Surfactants | 2.82 | 2.82 |
| Waxy alcohols | 4.0 | 4.0 |
| Emulsifier | 0.5 | 0.5 |
| Hair conditioner (Mineral Oil) | 0.5 | 0.5 |
| Preservative | 0.1 | 0.1 |
| Perfume (Fragrance) | 0.4 | 0.4 |
| pH Modifier (50% NaOH or Citric Acid) | 0.005 | 0.005 |
| Quaternary Ammonium Compound (PEG-2 Dimeadowfoam-Amidoethylmonium Methosulfate) | — | 0.25 |
| Total | 100.0 | 100.0 |

To evaluate each of the compositions (1) and (2), twelve European virgin hair tresses each having about 3.5 grams of hair and about 20 to about 22 cm in length were pre-cleaned and randomly separated into two sets of six tresses. The first set of six tresses was treated with 0.5 mL of the control (1) and the second set of six tresses was treated with 0.5 mL of the hair care composition with the PEG-2 dimeadowfoam-amidoethylmonium methosulfate (2). To treat each of the tresses, the respective composition (1) and (2) was manually massaged into the tress from root to tip for one minute, then rinsed under tap water. A curl setting was made with a plastic rod and dried overnight. After drying, all the tresses were exposed to a humidity controlled walk-in chamber maintained at 60% relative humidity (RH) and 25° C. for 24 hours.

Photocopies or photographs of each of the tresses were taken immediately after drying to provide the baseline ($T_0$), and after exposure to the humidity controlled walk-in chamber for 24 hours ($T_{24}$). The images were scanned and digitally analyzed to calculate the percentage change in area, % Δ Area, (i.e., degree of frizziness) comparing the square area (in pixels) of the baseline (i.e., after drying) and the final images (i.e., after exposure to the humidity walk-in chamber). The % Δ Area of each of the tresses was then calculated according to formula (3) and averaged for each set of six tresses. The results are summarized in Tables 2 and 3. Table 2 observed the volume of the area of the curl and "flyaways" (frizz or stray hairs). Table 3 only observed the volume of the curl.

$$\% \Delta \text{Area (degree of frizz)} = [(T_{24}-T_0)/T_0] \times 100 \quad (3)$$

TABLE 2

Curl Retention after 24 h at 60% RH and 25° C.

| Sample | % Δ Area |
|---|---|
| Control (1) | 40.39 |
| Test Composition (2) | 18.88 |
| % Less Frizziness of Test Composition (2) as compared to Control (1) | 53.27 |

TABLE 3

Curl Retention after 24 h at 60% RH and 25° C.

| Sample | % Δ Area |
|---|---|
| Control (1) | 31.19 |
| Test Composition (2) | 19.25 |
| % Curl Volume of Test Composition (2) as compared to Control (1) | 38.29 |

As illustrated in Tables 2 and 3, hair treated with the hair care composition (2) exhibited less change in frizziness and curl volume as compared to the control (1). Accordingly, hair treated with the hair care composition (2) exhibited relatively greater curl retention as compared to the control hair care composition (1) without the quaternary ammonium compound.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A hair care composition for reducing frizziness in hair of a subject, consisting of:
   Purified water
   Thickener
   Surfactants
   Waxy alcohols
   Emulsifier
   Mineral oil
   Preservative
   Perfume
   50% NaOH or citric acid
   about 0.25% of PEG-2 Dimeadowfoam-Amidoethylmonium Methosulfate.

2. The hair care composition of claim 1, wherein about 0.25% of PEG-2 Dimeadowfoam-Amidoethylmonium Methosulfate is present effective to reduce frizziness in the hair of the subject to about 53.27% frizziness as compared to the hair treated with a composition without about 0.25% of PEG-2 Dimeadowfoam-Amidoethylmonium Methosulfate.

3. A method for improving curl retention in hair of a subject, comprising contacting the hair care composition of claim 1.

4. The method of claim 3, wherein the hair contacted with the hair care composition exhibits relatively less change in curl volume as compared to hair treated with a hair care composition without about 0.25% of PEG-2 Dimeadowfoam-Amidoethylmonium Methosulfate.

5. A method for reducing frizziness in hair of a subject, comprising contacting the hair care composition of claim 1.

6. The method of claim 5, wherein the hair contacted with the hair care composition exhibits relatively less change in frizziness as compared to hair treated with a hair care composition without about 0.25% of PEG-2 Dimeadowfoam-Amidoethylmonium Methosulfate.

* * * * *